(12) United States Patent
Chi et al.

(10) Patent No.: US 7,112,690 B2
(45) Date of Patent: Sep. 26, 2006

(54) VOLATILE NOBLE METAL ORGANOMETALLIC COMPLEXES

(75) Inventors: Yun Chi, Hsinchu (TW); Yao-Lun Chen, Hsinchu (TW); Chao-Shiuan Liu, Taipei (TW); Yi-Hwa Song, Taichung (TW); Ying-Hui Lai, Nantou (TW); Arthur J. Carty, Ottawa (CA)

(73) Assignees: National Research Council of Canada, Ottawa (CA); National Tsing Hua University, Hsinchu (TW)

( * ) Notice: Subject to any disclaimer, the term of this patent is extended or adjusted under 35 U.S.C. 154(b) by 143 days.

(21) Appl. No.: 10/495,073

(22) PCT Filed: Nov. 8, 2002

(86) PCT No.: PCT/CA02/01721

§ 371 (c)(1),
(2), (4) Date: Oct. 8, 2004

(87) PCT Pub. No.: WO03/040150

PCT Pub. Date: May 15, 2003

(65) Prior Publication Data

US 2005/0033075 A1    Feb. 10, 2005

Related U.S. Application Data

(60) Provisional application No. 60/331,157, filed on Nov. 9, 2001.

(51) Int. Cl.
*C07F 15/00*    (2006.01)
*C23C 16/00*    (2006.01)

(52) U.S. Cl. ...................... 556/40; 556/137; 427/248.1; 427/587; 427/593

(58) Field of Classification Search .................. 556/40, 556/137; 427/248.1, 587, 593
See application file for complete search history.

(56) References Cited

OTHER PUBLICATIONS

Xu et al., Chemical Materials, vol. 10, pp. 2329-2331 (Aug. 15, 1998).*

* cited by examiner

*Primary Examiner*—Porfirio Nazario-Gonzalez
(74) *Attorney, Agent, or Firm*—J. Wayne Anderson

(57) ABSTRACT

A series of noble metal organometallic complexes of the general formula (I): $ML_aX_b(FBC)_c$, wherein M is a noble metal such as iridium, ruthenium or osmium, and L is a neutral ligand such as carbonyl, alkene or diene; X is an anionic ligand such as chloride, bromide, iodide and trifluoroacetate group; and FBC is a fluorinated bidentate chelate ligand such as beta diketonate, beta-ketoiminate, amino-alcoholate and amino-alcoholate ligand, wherein a is an integer of from zero (0) to three (3), b is an integer of from zero (0) to one (1) and c is an 10 integer of from one (1) to three (3). The resulting noble metal complexes possess enhanced volatility and thermal stability characteristics, and are suitable for chemical vapor deposition(CVD) applications. The corresponding noble metal complex is formed by treatment of the FBC ligand with a less volatile metal halide. Also disclosed are CVD methods for using the noble metal complexes as source reagents for deposition of noble metal-containing films such as Ir, Ru and Os, or even metal oxide film materials $IrO_2$, $OsO_2$ and $RuO_2$.

21 Claims, 4 Drawing Sheets

VOLATILE NOBLE METAL ORGANOMETALLIC COMPLEXES

This application is a National Stage application of PCT/CA02/01721 filed Nov. 8, 2002 which claims benefit of U.S. Provisional Application 60/331,157 filed Nov. 9, 2001.

BACKGROUND OF THE INVENTION

1. Field of the Invention

The present invention relates to a series of novel volatile noble metal organometallic complexes, and to a method for the preparation thereof. Such complexes are particularly useful as chemical vapor deposition (CVD) precursors for formation of noble metal-containing thin films on substrate assemblies.

2. Description of the Prior Art

Chemical vapor deposition (hereafter indicated as "CVD") is widely used for the deposition of noble metal-containing thin films on a variety of substrate assemblies. CVD is a particularly attractive method for forming thin film coatings in the semiconductor industries because it has the ability to readily control the composition of the thin film and to form a thin film layer without contamination of, or damage to the substrate assembly. CVD may also be applied to deposit the desired thin film into holes, trenches, and other stepped structures. In situations where conformal thin film deposition is required, CVD would also be a preferred method, since evaporation and sputtering techniques cannot be used to form a conformal thin-film layer. However, CVD processes require suitable source reagents that are sufficiently volatile to permit a rapid transport of their vapors into the CVD reactor. The source reagents, which may be called the precursors, should be relatively stable and inert against oxygen and moisture in air at room temperature to allow long-term storage. They also should decompose cleanly in the CVD reactor to deposit a high purity metal component at the desired growth temperature on the substrate assembly.

The tris-acetylacetonato and tris-allyl iridium(III) complexes $Ir(acac)_3$ and $Ir(C_3H_5)_3$ are two commonly known CVD precursors, for which the commercially available $Ir(acac)_3$ is a better choice due to its excellent air stability. However the high melting point and low volatility of $Ir(acac)_3$ has limited its development as the industrial standard. In addition, other source reagents consist of Ir(I) metal complexes such as Ir(COD)(MeCp), COD=1,4-cyclooctadiene and MeCp=methylcyclopentadienyl, Ir(COD)(hfac), hfac=hexafluoroacetylacetonate, Ir(COD)(amak), amak=$OC(CF_3)_2CH_2NMe_2$, $[Ir(COD)(\mu\text{-OMe})]_2$, $[Ir(COD)(\mu\text{-OAc})]_2$, OAc=acetate, and $[Ir(CO)_2(\mu\text{-SBu}^t)]_2$. For this family of iridium CVD precursors, the monomeric metal complexes Ir(COD)(MeCp) and Ir(COD)(hfac) appear to be more useful for iridium deposition due to their enhanced volatility and vapor phase transport properties which are uncomplicated by monomer-dimer equilibria. The physical properties of these iridium CVD precursors are listed in Table 1.

The chemical vapor deposition of osmium was achieved using the commercially available osmocene $(C_5H_5)_2Os$, osmium tetraoxide $OsO_4$, or even the metal carbonyl complexes such as $Os(CO)_5$, $Os_3(CO)_{12}$, $Os(CO)_4(hfb)$, where hfb=hexafluoro-2-butyne, and the tailor-made precursor complexes $Os(CO)_4I_2$, $Os(CO)_3(tfa)(hfac)$, tfa=trifluoroacetate, and even $[Os(CO)_3(hfpz)]_2$, hfpz=3,5-bis(trifluoromethyl) pyrazolate. Osmium-containing thin films with reasonable purity were obtained in most of these studies; however, the usage of these source reagents has encountered difficulties such as the greater toxicity for $OsO_4$, poor thermal stability for $Os(CO)_5$, and lower gas phase transportation capability for the osmocene complex $(C_5H_5)_2Os$ and polynuclear metal complex $Os_3(CO)_{12}$.

Moreover, the known ruthenium CVD precursor complexes include ruthenocene, $Ru(C_5H_5)_2$, and its alkyl substituted complexes, such as $Ru(C_5H_4Et)_2$, carbonyl complexes, such as $Ru(CO)_4(hfb)$, hfb=hexafluoro-2-butyne, $Ru(CO)_2(hfac)_2$ and $Ru_3(CO)_{12}$; tris-β-diketonate complexes, such as $Ru(acac)_3$, $Ru(tfac)_3$ and $Ru(tmhd)_3$; and organometallic olefin complexes, such as bis(2,4-dimethylpentadienyl)ruthenium, bis(2,4-dimethyloxapentadienyl)ruthenium, $Ru(\eta^6\text{-}C_6H_6)(\eta^4\text{-}C_6H_8)$, $C_6H_8$=1,3-cyclohexadiene, and $Ru(COD)(C_3H_5)_2$, COD=1,5-cyclooctadiene. Selected physical properties of these known osmium and ruthenium organometallic reagents are listed in Table 2.

Accordingly, there is a continuing need for highly volatile and relatively air and thermally stable CVD source reagents for various CVD applications, such as the formation of bottom electrodes, diffusion barriers, conductors, superconductors, dielectrics, capacitors, protective coatings and catalytic metal alloy films. More specifically, the iridium as well as the ruthenium source materials are becoming important for fabricating metallic iridium and ruthenium, iridium oxide ($IrO_2$) and ruthenium oxide ($RuO_2$) that have recently gained interest for use as bottom electrodes in both dynamic random access memories (DRAMs) and for ferroelectric-based memory devices (FRAMs), which incorporate perovskite metal oxides as the capacitor layer. Such perovskite dielectric materials include SBT, BST, PZT, PLZT, etc., wherein SBT=strontium bismuth tantalite, BST=barium strontium titanate, PZT=lead zirconium titanate and PLZT=lead lanthanum zirconium titanate. The practical advantages of iridium and ruthenium based materials over other electrode materials include ease of deposition, good adhesion to Si wafer, the ability to form a stable conducting oxide at high temperatures in an oxidizing environment, and the ability to operate at high temperatures in a working device. On the other hand, osmium CVD source reagents may find application in replacing the relatively less stable source reagent $Os(CO)_5$ or the highly toxic compound $OsO_4$ for making the osmium-coated thermionic cathodes and abrasive-resistant osmium hard-coatings.

Generally speaking, CVD of these metal-containing thin film coatings has been limited due to a variety of reasons, including formation of poor film quality, requiring of high processing temperatures, lack of suitable precursor compounds, and instability of the precursors used in the deposition systems. The availability of suitable precursors with moderate volatility and stability appears to be the greatest limiting factors in the CVD applications, as the poor stability against heat and moisture makes them difficult to store and handle, yields inferior thin film coatings and creates serious contamination at the as-deposited thin films in production-scale operations.

It is therefore an object of the present invention to provide suitable novel CVD precursors that are amenable to use in the chemical vapor deposition of noble metal-containing films.

Based on the need for these noble metal-containing coatings, the prior art has sought to provide new design for the suitable CVD precursors and continued to seek improvements in their basic physical properties that are advantageous for integration with current CVD technology.

It is another object of the present invention is to provide a simplified CVD method for forming a noble metal-containing film on a substrate assembly utilizing these newly prepared precursors. Other objects, features, and advantages will be more fully apparent from the ensuing disclosure and appended claims.

TABLE 1

Selected physical properties of known iridium CVD precursors

| Compound | M.P. (° C.) | CVD $T_D$ (° C.) | Sublimation Condition | References |
|---|---|---|---|---|
| Ir(acac)$_3$ | | 300–400° C. | subl. at 180–200° C. | (a) |
| Ir(C$_3$H$_5$)$_3$ | dec. at 65° C. | 100° C. | subl. at 50° C./15 torr | (b) |
| Ir(COD)(MeCp) | 38–40° C. | 270–350° C. | subl. at 95° C./0.05 torr | (c) and (d) |
| Ir(COD)(hfac) | 120° C. | 250–400° C. | subl. at 60° C./0.05 torr | (e) |
| Ir(COD)(amak) | 127° C. | 350° C. | subl. at 50° C./0.2 torr | (f) |
| [Ir(COD)(μ-OAc)]$_2$ | 135° C. | 250° C. | subl. at 125° C./0.07 torr | (c) |
| [Ir(CO)$_2$(μ-SBu$^t$)]$_2$ | 128° C.; dec. 160° C. | 150–450° C. | subl. at 80–140° C./0.1 torr | (f) |

Abbreviations:
$T_D$ = deposition temperature,
acac = acetylacetonate,
C$_3$H$_5$ = allyl,
MeCp = methylcyclopentadienyl,
hfac = hexafluoroacetylacetonate,
amak = OC(CF$_3$)$_2$CH$_2$NMe$_2$,
COD = 1,5-cyclooctadiene,
OAc = acetate.
(a) Sun, Y.-M.; Endle, J. P.; Smith, K.; Whaley, S.; Mahaffy, R.; Ekerdt, J. G.; White, J. M.; Hance, R. L. Thin Solid Films 1999, 346, 100.
(b) Kaesz, H. D.; Williams, R. S.; Hicks, R. F.; Zink, J. I.; Chen, Y.-J.; Muller, H.-J.; Xue, Z.; Xu, D.; Shuh, D. K.; Kim, Y. K. New. J. Chem. 1990, 14, 527.
(c) Hoke, J. B.; Stern, E. W.; Murray, H. H. J. Mater. Chem. 1991, 1, 551.
(d) Sun, Y.-M.; Yan, X.-M.; Mettlach, N.; Endle, J. P.; Kirsch, P. D.; Ekerdt, J. G.; Madhukar, S.; Hance, R. L.; White, J. M. J. Vac. Sci. Technol. 2000, 18, 10.
(e) Xu, C.; Baum, T. H.; Rheingold, A. L. Chem. Mater. 1998, 10, 2329.
(f) Chen, Y.-L.; Liu, C.-S.; Chi, Y.; Carty, A. J.; Peng, S.-M.; Lee, G.-H. Chem. Vap. Deposition 2002, 8, 17.
(g) Serp, P.; Feurer, R.; Kalck, P.; Gomes, H.; Faria, J. L.; Figueiredo, J. L. Chem. Vap. Deposition 2001, 7, 59.

TABLE 2

Relevant physical properties of selective known osmium and ruthenium CVD precursors

| Compound | M.P. (° C.) | CVD $T_D$ (° C.) | Relative volatility | References |
|---|---|---|---|---|
| Osmocene | 194–198 | 350–500° C. | | (a) |
| Os$_3$(CO)$_{12}$ | 226–228° C. | 225° C. | vaporized at 50° C. | (b) |
| Os(CO)$_4$(hfb) | | 600° C. | subl. at 25° C./0.05 torr | (c) |
| Os(CO)$_4$I$_2$ | | 450–550° C. | subl. at 55° C./0.45 torr | (d) |
| Os(CO)$_3$(tfa)(hfac) | 153–156° C. | 400–500° C. | subl. at 55° C./0.45 torr | (d) |
| [Os(CO)$_3$(hfpz)]$_2$ | 189° C. | 400–550° C. | vaporized at 110° C. | (e) |
| Ruthenocene | 194–198 | 225–500° C. | vap. pressure 0.01 torr at 85° C. | (a) and (f) |
| Ru$_3$(CO)$_{12}$ | 150 dec. | 150–175° C. | vaporized at 50° C. | (b) |
| Ru(CO)$_4$(hfb) | | 200–500° C. | subl. at 25° C./0.05 torr | (c) |
| Ru(tmhd)$_3$ | 210–213 | 250–600° C. | subl. at 120° C./0.5 torr | (g) |
| Ru(COD)(C$_3$H$_5$)$_2$ | | 300° C. | vaporized at 75° C. | (h) |
| Ru(CO)$_2$(hfac) | 55–75° C. | 400° C. | vaporized at 50° C. | (i) |
| RuO$_4$ | 27° C. | 150–220° C. | b.p. = 129° C. | highly toxic, (j) |

Abbreviation:
$T_D$ = deposition temperature,
hfb = hexafluoro-2-butyne,
tfa = trifluoroacetate,
hfac = hexafluoroacetylacetonate,
hfpz = 3,5-bis(trifluoromethyl) pyrazolate,
tmhd = 2,2,6,6-tetramethyl-3,5-heptanedionate,
C$_3$H$_5$ = allyl and
COD = 1,5-cyclooctadiene.
(a) Smart, C. J.; Gulhati, A.; Reynolds, S. K. Mater. Res. Soc. Symp. Proc. 1995, 363, 207.
(b) Boyd, E. P.; Ketchumn, D. R.; Deng, H.; Shore, S. G. Chem. Mater. 1997, 9, 1154.
(c) Seuzaki, Y.; Gladfelter, W. L.; McCormick, F. B. Chem. Mater. 1993, 5, 1715.
(d) Yu, H.-L.; Chi, Y.; Liu, C.-S.; Peng, S.-M.; Lee, G.-H. Chem. Vap. Deposition 2001, 7, 245.
(e) Chi, Y.; Yu, H.-L.; Cling, W.-L.; Liu, C.-S.; Chen, Y.-L.; Chou, T.-Y.; Peng, S.-M.; Lee, G.-H. J. Mater. Chem. 2002, 12, 1363.
(f) Park, S.-E.; Kim, H.-M.; Kim, K.-B.; Min, S.-H. J. Electrochem. Soc. 2000, 147, 203.
(g) Vetrone, J.; Foster, C. M.; Bai, G.-R.; Wang, A.; Patel, J.; Wu, X. J. Mater. Res. 1998, 13, 2281.
(h) Barreca, D.; Buchberger, A.; Daolio, S.; Depero, L. E.; Fabrizio, M.; Morandini, F.; Rizzi, G. A.; Sangaletti, L.; Tondello, E. Langmuir 1999, 15, 4537.
(i) Lee, F.-J.; Chi, Y.; Hsu, P.-F.; Chou, T.-Y.; Liu, C.-S.; Peng, S.-M.; Lee, G.-H. Chem. Vap. Deposition 2001, 7, 99.
(j) Sankar, J.; Sham, T. K.; Puddephatt, R. J. J. Mater. Chem., 1999, 9, 2439.

SUMMARY OF THE INVENTION

According to one aspect of the invention we provide, a novel noble metal organometallic complex of general formula (I):

[ML$_a$X$_b$(FBC)$_c$]     (I)

wherein M is a noble metal; L is a neutral ligand selected from the group consisting of carbonyl, alkene, diene and derivatives of alkenes and dienes additionally containing alkyl or fluorinated alkyl substituents; X is an anionic ligand such as chloride, bromide, iodide and trifluoroacetate group; wherein a is an integer of from zero (0) to three (3), b is an integer of from zero (0) to one (1) and c is an integer of from one (1) to three (3); FBC ligand is a fluorinated bidentate chelate ligand such as a beta-diketonate (FBC1), beta-ketoiminate (FBC2), imino-alcoholate (FBC3) and amino-alcoholate (FBC4) having the structural formula indicated below:

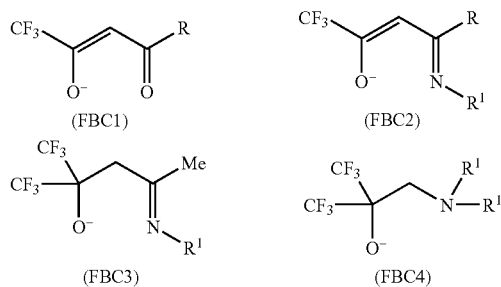

wherein R is a C1–C4 alkyl group such as methyl and t-butyl, or trifluoromethyl; R$^1$ is a C1–C6 alkyl group e.g. methyl, ethyl, allyl, n-propyl, i-propyl, n-butyl and i-butyl, which may be substituted by a C1–C4 alkoxy group, and wherein FBC4, one of the R$^1$ groups may be H.

It will be appreciated by those skilled in the art that, having established by example that the nitrogen atom of the FBC4 ligand requires two R$^1$ groups to fulfill its trivalent structure, that one of the R$^1$ groups can be replaced by a hydrogen atom, because of the similar chemical behavior between hydrogen atoms and alkyl substituents in this system.

The noble metal is preferably iridium, ruthenium or osmium.

According to another aspect of the invention, we provide a method for making a novel noble metal organometallic complex of general formula (I), comprising (a) reacting the respective FBC ligand with a suitable metal hydride e.g. sodium hydride, followed by (b) treatment of the product so formed with a metal halide salt of the desired metal.

The preferred metal halide salts include [Ir(COD)(μ-Cl)]$_2$, COD=1,5-cyclooctadiene, [Os(CO)$_3$(μ-X)]$_2$, X=CF$_3$CO$_2$, Cl, Br and I, [Ru(COD)Cl$_2$]$_x$ and [Ru(NBD)Cl$_2$]$_x$, COD=1, 5-cyclooctadiene and NBD=2,5-norbornadiene.

The FBC ligands are characterized in that they are highly fluorinated and contain oxygen or nitrogen donor atoms. Despite the obvious difference in their structural design, this class of ligand can be covalently coordinated to the central metal atom to form the stable chelate interaction. The ligand fragment "(FBC1)" represents the typical fluorinated beta-diketonate group, wherein R is a C1–C4 alkyl group e.g. methyl, t-butyl, or trifluoromethyl; R$^1$ is a C1–C6 alkyl group e.g. methyl, ethyl, allyl, n-propyl, i-propyl, n-butyl and i-butyl, or 2-methoxyethyl. The second ligand fragment "(FBC2)" represents the beta-ketoiminate fragment which can be prepared from the reaction of neutral (BFC1)H with an organic amine H$_2$NR$^1$ in the presence of a solid acid catalyst such as montmorillonite K10. The third and the fourth ligand group "(BFC3)" and "(BFC4)" belong to a new class of fluoroalcohol molecules with a pendant amine that can bend back and forming a strong dative interaction to the central metal atom, and are prepared according to literature methods. Moreover, because of the presence of at least one electronegative trifluoromethyl (CF$_3$) substituent on each of the FBC ligands, the ligands as well as the resulting metal complexes are chemically stable and can be easily volatilized into the gas phase. It is well understood that the CF$_3$ substituents have the capability to reduce the Van der Waals interactions between individual molecules and hence lower the boiling or sublimation temperature of the complex.

The respective ligands are either purchased from the commercial supplier or synthesized according to the literature procedures.

In another aspect, the invention relates to the use of the novel noble metal organometallic complex of the general formula ML$_a$X$_b$(FBC)$_c$ (I) as a source reagent for chemical vapor deposition(CVD) applications. Thus, the noble metal complex is charged into a source reservoir of a CVD reactor to deposit the noble metal-containing thin-film on a substrate assembly.

In accordance with the invention, the iridium, ruthenium or osmium thin film material is formed on the substrate by depositing any one of the novel iridium, ruthenium or osmium source reagents of formula I under an inert atmosphere, such as N$_2$, He or Ar, or in the presence of reducing carrier gas such as H$_2$. The resulting iridium, ruthenium or osmium layer may be converted to IrO$_2$, RuO$_2$ or OsO$_2$ thin film in an oxygen-containing atmosphere at the elevated temperature. In a like manner, the IrO$_2$, RuO$_2$ or OsO$_2$ thin film material may be prepared by depositing either one of the iridium, ruthenium or osmium source reagents on the substrate under the oxygen-containing atmosphere or under the condition where an oxygen-containing plasma is applied.

Such chemical vapor deposition conditions may advantageously comprise the presence of the gaseous co-reagent or carrier gas commonly utilized in CVD applications. For example, the employment of an inert gas atmosphere or a slow stream of inert carrier gas such as N$_2$, He and Ar, or a reducing carrier gas such as H$_2$, favors the formation of pure iridium, ruthenium and osmium thin films on substrates. On the other hand, the introduction of high concentrations of an oxygen-containing atmosphere or oxidizing carrier gas such as O$_2$, or N$_2$O may lead to the formation of Ir/IrO$_2$ mixture, Ru/RuO$_2$ mixture, Os/OsO$_2$ mixture or even high purity IrO$_2$, RuO$_2$ or OsO$_2$ films at a higher deposition temperature, or upon increasing the deposition time as well as the partial pressure of the oxidizing carrier gas.

DETAILED DESCRIPTION OF THE INVENTION

A. Iridium Precursors

Figure 1:
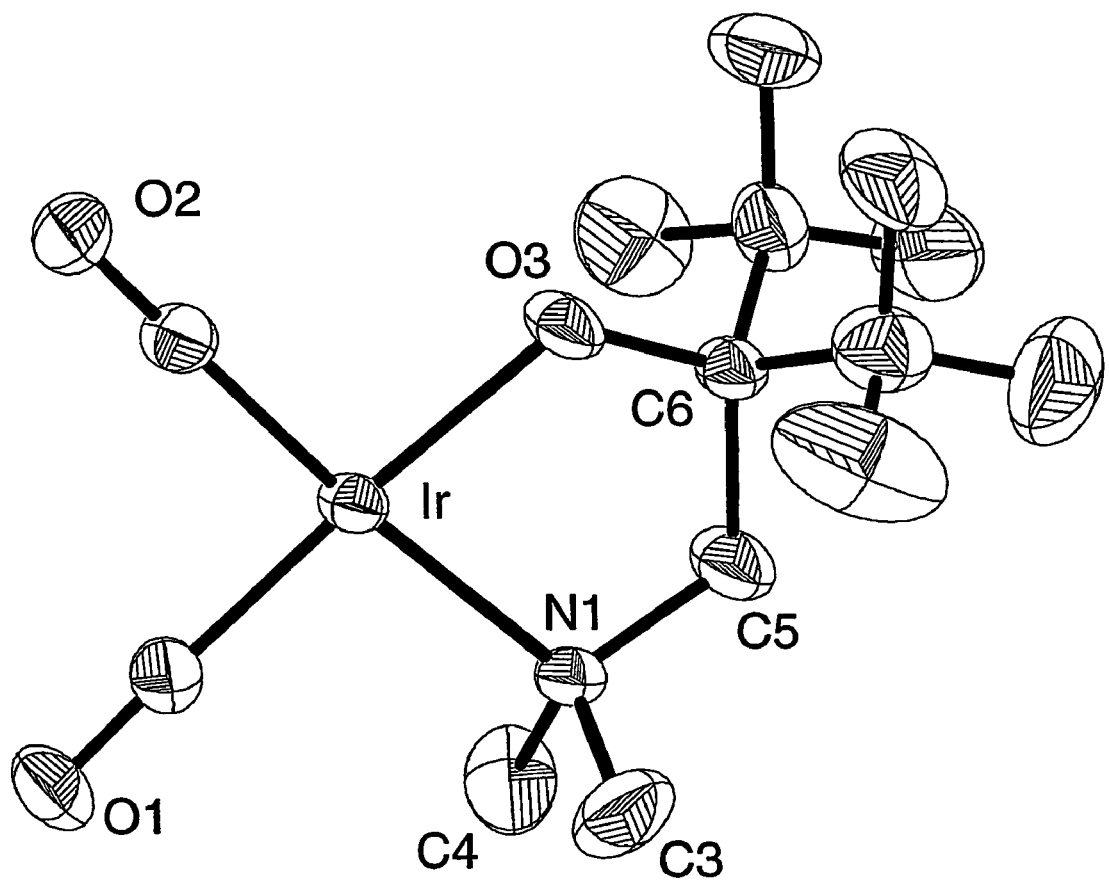
FIG. 1 is a three-dimensional illustration of an iridium complex [Ir(CO)$_2$(FBC4)] according to the invention.

In the present invention, neutral iridium precursors are chosen from a general class of compound of formula (II) (III) and (IV):

$$[IrL_a(FBC2)] \quad (II),$$

$$[IrL_a(FBC3)] \quad (III)$$

and

$$[IrL_a(FBC4)] \quad (IV)$$

wherein L is a neutral ligand selected from the group consisting of carbonyl, alkene, diene or derivatives of alkenes and dienes additionally containing at least one alkyl or fluorinated alkyl substituent; a is an integer of one or two, depending on the donor bonding of the selected ligand; FBC2 ligand is a fluorinated bidentate chelate ligand such as a beta-ketoiminate, imino-alcoholate (FBC3) and amino-alcoholate (FBC4) having the structural formula indicated below:

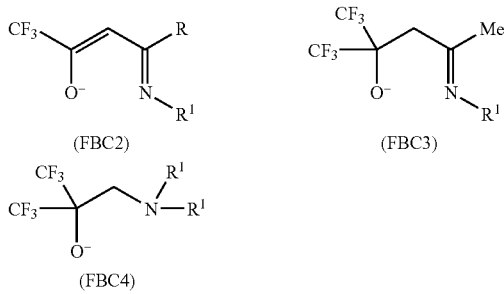

wherein R is C1–C4 alkyl, e.g. methyl or t-butyl, or trifluoromethyl; $R^1$ is C1–C6 alkyl e.g. methyl, ethyl, allyl, n-propyl, i-propyl, n-butyl or i-butyl, which may be substituted by a C1–C4 alkoxy group e.g. 2-methoxyethyl, and wherein FBC4, one of the $R^1$ groups may be H.

It will be appreciated by those skilled in the art that, having established by example that the nitrogen atom of the FBC4 ligand requires two $R^1$ groups to fulfill its trivalent structure, we can substitute one of the $R^1$ groups by a hydrogen atom, because of the similar chemical behavior between a hydrogen atom and an alkyl substituent in this system.

Broadly, iridium complexes of formula (II), (III) and (IV) may be prepared by the direct chloride exchange reaction as show in equations [1], [2] and [3]:

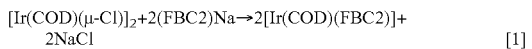
$$[Ir(COD)(\mu\text{-}Cl)]_2 + 2(FBC2)Na \rightarrow 2[Ir(COD)(FBC2)] + 2NaCl \quad [1]$$

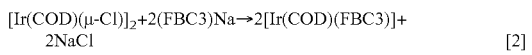
$$[Ir(COD)(\mu\text{-}Cl)]_2 + 2(FBC3)Na \rightarrow 2[Ir(COD)(FBC3)] + 2NaCl \quad [2]$$

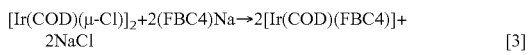
$$[Ir(COD)(\mu\text{-}Cl)]_2 + 2(FBC4)Na \rightarrow 2[Ir(COD)(FBC4)] + 2NaCl \quad [3]$$

Thus, the neutral ligand "$L_a$" of formula (II), (III) and (IV) in this case is the COD ligand, in which both of the alkene functional groups form strong bonding interactions to the central iridium atom. In addition, subsequent treatment of [Ir(COD)(FBC2)], [Ir(COD)(FBC3)] or [Ir(COD)(FBC4)] with carbon monoxide atmosphere at elevated temperature gives the corresponding CO substituted complex $[Ir(CO)_2(FBC2)]$, $[Ir(CO)_2(FBC3)]$ or $[Ir(CO)_2(FBC4)]$, respectively; and the COD ligand is now replaced by two carbon monoxide ligands; the stoichiometric transformation is indicated in the following equations [4], [5] and [6].

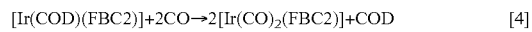
$$[Ir(COD)(FBC2)] + 2CO \rightarrow 2[Ir(CO)_2(FBC2)] + COD \quad [4]$$

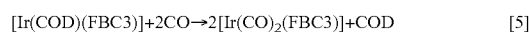
$$[Ir(COD)(FBC3)] + 2CO \rightarrow 2[Ir(CO)_2(FBC3)] + COD \quad [5]$$

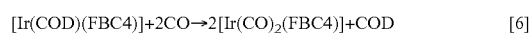
$$[Ir(COD)(FBC4)] + 2CO \rightarrow 2[Ir(CO)_2(FBC4)] + COD \quad [6]$$

As a result, the neutral ligand "L" of formula (II), (III) and (IV) represents a CO ligand and a is now two (2). Selected physical properties of these iridium complexes are summarized in Table 3. It is important to note that these iridium complexes $[IrL_a(FBC2)]$ (II), $[IrL_a(FBC3)]$ (III) and $[IrL_a(FBC4)]$ (IV) are all relatively stable at room temperature in air and they can be handled in the absence of an inert atmosphere such as nitrogen and argon. The ability to vary the substituents on all three FBC ligands provides an excellent degree of control over both volatility and the deposition parameters for the respective CVD experiments. Moreover, replacement of COD with two carbonyl ligands has substantially increased the volatility and stability of these precursor compounds. Thus, the choice of the "$L_a$" groups can also have a significant influence on their basic properties.

A single crystal X-ray diffraction study of compound $[Ir(CO)_2(FBC4)]$ with the substituents $R^1$=Me was carried out, revealing the square planar arrangement of the iridium metal center alone with two cis-CO ligands and the corresponding fluorinated bidentate chelate ligand. The ORTEP representation of the molecular structure is shown in FIG. 1.

Specifically, the molecular structure of the complex $[Ir(CO)_2(FBC4)]$ with $R^1$=Me; selected bond distances: Ir—C1=1.818 Å, Ir—C2=1.838 Å, Ir—O1=1.990 Å, Ir—N1=2.132 Å, selected bond angles: C1-Ir—C2=88.73°, C1-Ir—O1=177.06°, C2-Ir—O1=94.07°, C1-Ir—N1=96.13°, C2-Ir—N1=175.13°, N1-Ir—O1=81.06°.

B. Ruthenium Precursors

The identical synthetic strategy can be extended to a reaction using the ruthenium halide compound $[RuL_aCl_2]_x$, and upon treatment with the respective fluorinated ligand salt FBC1)Na, (FBC4)Na and (FBC2)Na, the neutral ruthenium precursors of formula (V), (VI) and (VII):

$$[RuL_a(FBC1)_2] \quad (V),$$

$$[RuL_a(FBC4)_2] \quad (VI)$$

and

$$[Ru(FBC2)_3] \quad (VII)$$

are obtained in moderate yields;

wherein L is a neutral ligand selected from the group consisting of a cyclic diene such as COD or NBD, or derivatives of a cyclic diene additionally containing at least one alkyl or fluorinated alkyl substituent; a is one or zero, depending on the (FBC) ligand selected for the reactions; FBC ligand is a fluorinated bidentate chelate ligand such as beta-diketonate (FBC1), beta-ketoiminate (FBC2) and amino-alcoholate (FBC4) having structural formula indicated below:

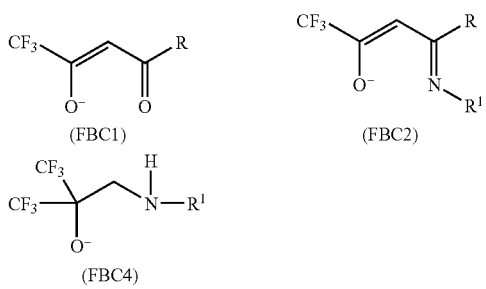

(FBC1)  (FBC2)

(FBC4)

wherein R is a C1–C4 alkyl group e.g. methyl, t-butyl and trifluoromethyl; $R^1$ is a C1–C6 alkyl group e.g. methyl, ethyl, allyl, n-propyl, i-propyl, 2-methoxyethyl, n-butyl and i-butyl. Moreover, it is important to note that the nitrogen atom of the aminoalcoholate ligand (FBC4) requires at least one hydrogen substituent; otherwise, no stable ruthenium product can be isolated.

Using the ruthenium complex $[Ru(COD)Cl_2]_x$ as an example to illustrate the previously discussed procedure, the ruthenium metal complexes of general formulas (V), (VI) and (VII) may be obtained by a direct reaction as shown in the following equations [7], [8] and [9]:

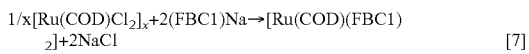  [7]

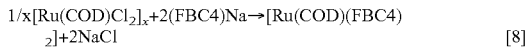  [8]

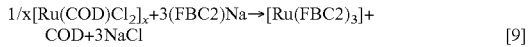  [9]

In addition, specific example of neutral ligand "L" of formula (V) and (VI) in this case include COD or NBD, i.e. 1,5-cyclooctadiene or 2,5-norbornadiene, in which the alkene C—C double bonds of the COD or NBD ligand are strongly coordinated to the ruthenium atom, while that of the formula (VII) shows the co-existence of three fluorinated bidentate chelate ligands (FBC2), without the neutral donor ligand residing in the coordination sphere of the ruthenium atom, as the ruthenium metal has inadvertently oxidized from +2 to +3 oxidation state during the reaction. Selected physical properties of these ruthenium complexes are summarized in Table 4.

Figure 2:
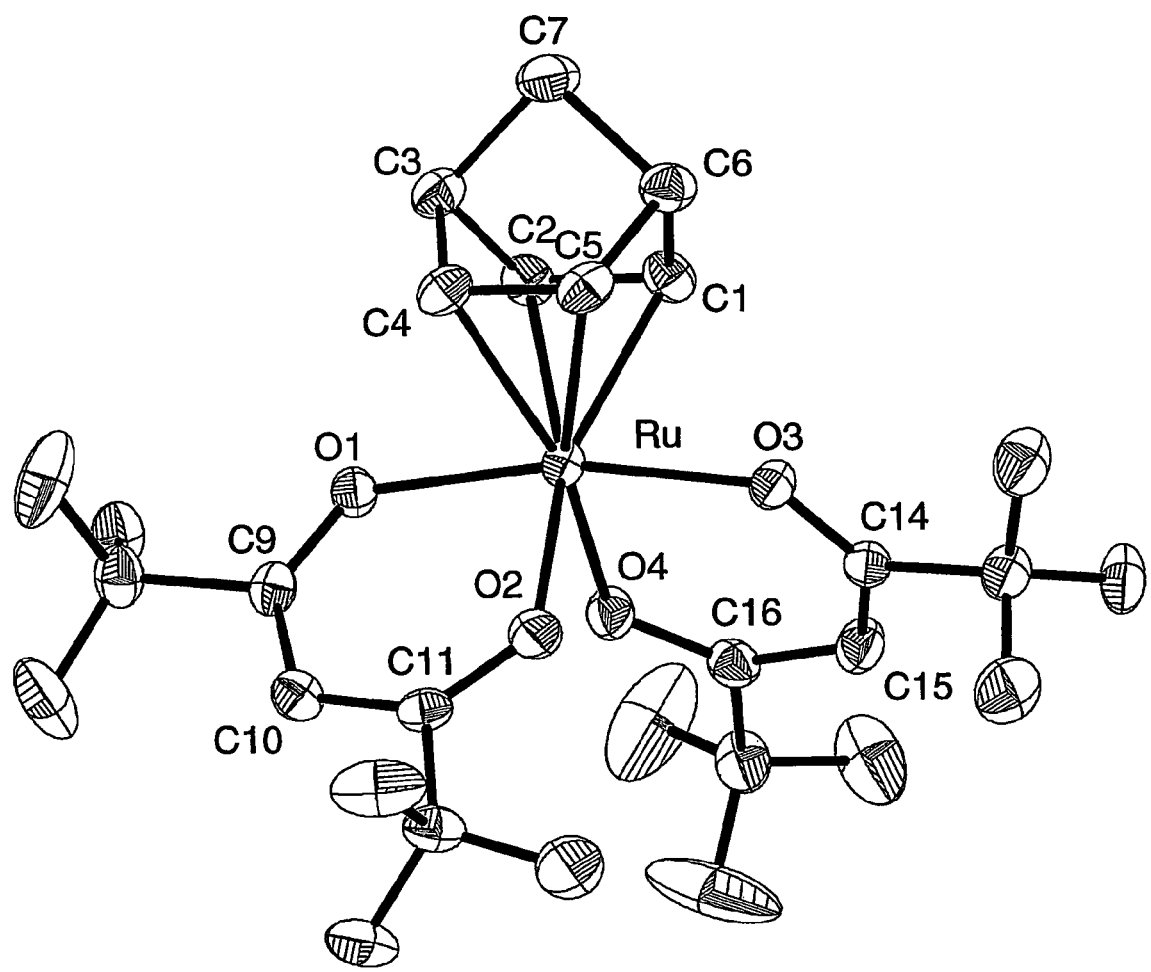
FIG. 2 is a three-dimensional illustration of a ruthenium complex [Ru(NBD)(FBC1)$_2$] with only two (FBC) ligands.

To further illustrate the feasibility of this invention, the structure of the complex $[Ru(NBD)(FBC1)_2]$ wherein $R=CF_3$ is confined by single crystal X-ray diffraction analysis (FIG. 2). It consists of an octahedral environment with one NBD and two hfac chelate ligands. Moreover, all Ru—O(hfac) bond distances are within a narrow range 2.077(2)~2.086(2) Å, exhibiting no obvious difference between the two dissimilar Ru—O fragments, the first is trans to the C—C double bond of the NBD ligand, while the other is trans to the second Ru—O(hfac) vector. This observation is in contrast to that of the carbonyl complex $[Ru(CO)_2(hfac)_2]$, in which the Ru—O distances trans to the CO ligand (2.075(2) and 2.081(2) Å) are found to be slightly longer than the other two Ru—O distances (2.050(2)~2.052(2) Å), showing a thermodynamic labilization effect imposed by the CO ligands.

Specifically, the molecular structure of the complex $[Ru(NBD)(FBC1)_2]$ with $R=CF_3$; selected bond distances: Ru—O1=2.083 Å, Ru—O2=2.084 Å, Ru—O3=2.077 Å, Ru—O4=2.086 Å, Ru—C1=2.183 Å, Ru—C2=2.178 Å, Ru—C4=2.189 Å, Ru—C5=2.187 Å, selected bond angles: O1-R—O3=167.40°, O3-R—O2=80.03°, O3-R—O4=89.90°, O3-R—O4=89.90°, O1-R—O2=89.57°, O1-R—O4=82.55°.

Figure 3:
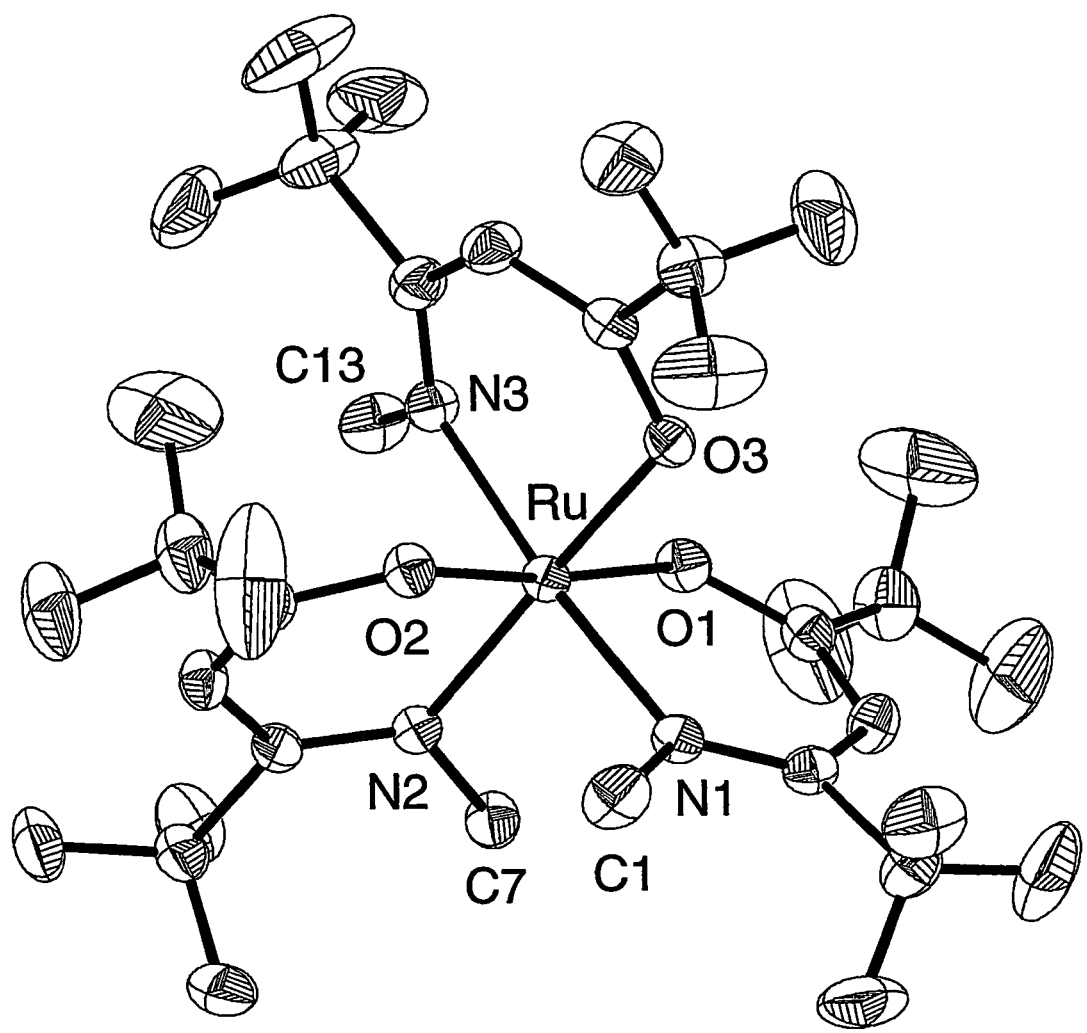
FIG. 3 is a three-dimensional illustration of a ruthenium complex [Ru(FBC2)$_3$] showing three (FBC2) ligands.

The structure of the second type of precursor complex with formula $[Ru(FBC2)_3]$ wherein $R=CF_3$ and $R^1=Me$, is also determined by X-ray diffraction analysis. As indicated in FIG. 3, the complex adopts an octahedral ligand arrangement, and the unsymmetrical bidentate chelate ligands are situated around the ruthenium atom to give the meridional geometry. This X-ray structure confirms that the asymmetric FBC2 ligand is capable of imposing the meridional geometry about the metal center, to the total exclusion of the facial isomer that would exhibit a large steric interaction between the $R^1$ substituent of all three FBC2 ligands.

Specifically, the structure of the precursor complex with formula $[Ru(FBC2)_3]$ with $R=CF_3$ and $R^1=Me$; selected bond distances: Ru—O1=2.015 Å, Ru—O2=1.984 Å, Ru—O3=2.013 Å, Ru—N1=2.090 Å, Ru—N2=2.037 Å, Ru—N3=2.042 Å, selected bond angles: O2-Ru—O1=174.45°, O3-Ru—N2=173.54°, N3-Ru—N1=174.00°.

C. Osmium Precursors

In yet another aspect of the invention, the osmium CVD precursors of the general formula (VIII):

  (VIII)

are obtained;

wherein L represents carbonyl ligand; a has a constant value of three, X is an anionic monodentate ligand such as chloride, bromide, iodide or trifluoroacetate, FBC ligand is a fluorinated bidentate chelate ligand such as a beta-diketonate group (FBC1). Preferred beta-diketonate ligands (ABCB) include: (hfac)=hexafluoroacetylacetonate, (tfac)=trifluoroacetylacetonate, and (tdhd)=1,1,1-trifluoro-5,5-dimethyl-2,4-hexanedionate.

A useful synthetic procedure for this compound involves direct heating of a mixture of osmium halide salt $[Os(CO)_3(\mu-X)]_2$ and at least two equivalents of the fluorinated chelate ligand (FBC1)H sealed in a Carius tube. The tube is then heated at 180° C. for 6 hours to ensure the completion of reaction. This process is best illustrated by the proposed stoichiometric transformation, as shown in equation [10]:

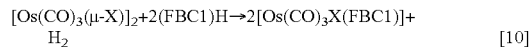  [10]

Due to the lower chemical reactivity of osmium compound $[Os(CO)_3(\mu-X)]_2$, three other fluorinated bidentate chelate ligands (FBC)H have failed to exhibit a similar reaction pattern and thus, afforded no isolable product that can serve as the required osmium CVD precursor. Moreover, all attempts to generate the complex of formula $[Os(CO)_2(FBC1)_2]$ by employing a large excess of the (FBC1) ligand have failed, and only afforded the known mono-substituted product $[Os(CO)_3X(FBC1)]$.

Figure 4:
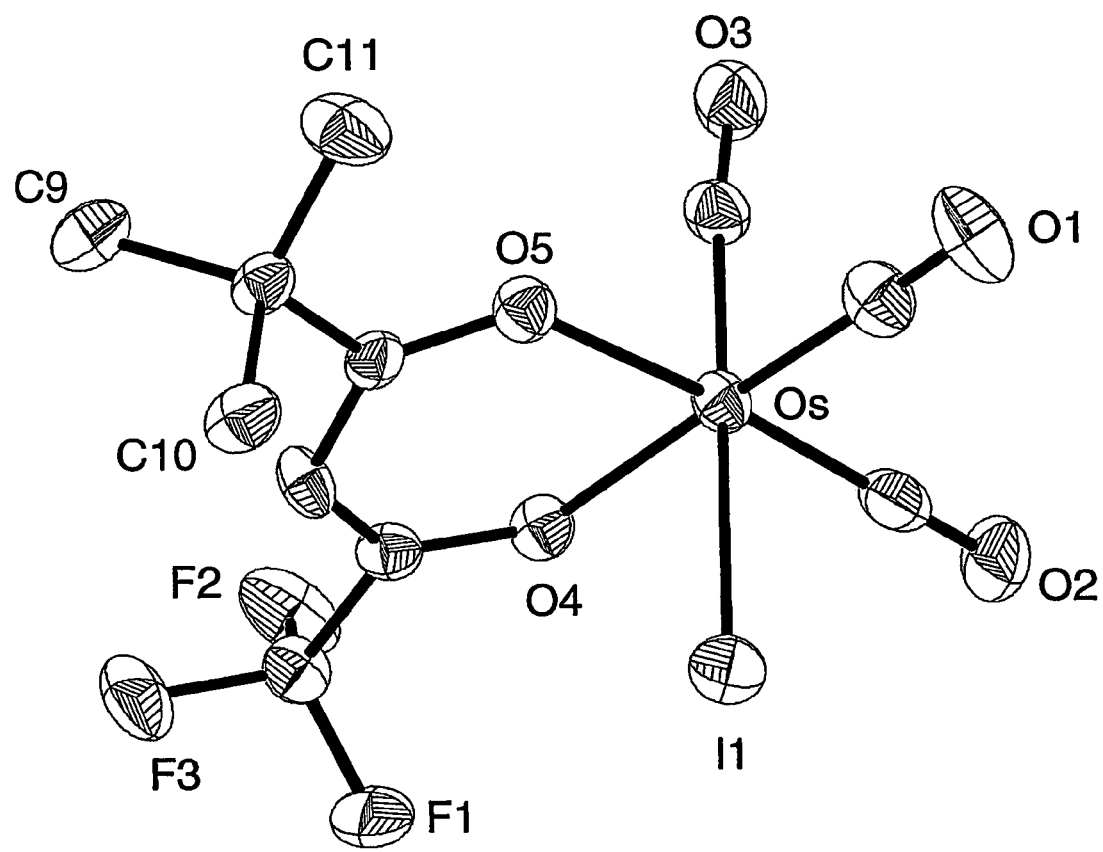
FIG. 4 is a three-dimensional illustration of an osmium complex [Os(CO)$_3$I(FBC1)] according to the invention.

The product complexes of formula $[Os(CO)_3X(FBC1)]$ are readily characterized using mass spectrometry (MS), nuclear magnetic resonance spectroscopy (NMR), infrared spectroscopy (IR), single crystal X-ray analysis, elemental analysis, and thermal gravimetric analysis (TGA). Selected physical properties of the ruthenium and osmium source reagents of the present invention are summarized in Table 5. The structure of the complex $[Os(CO)_3I(FBC1)]$ where $R^1=$t-butyl is determined by single crystal X-ray diffraction. Its ORTEP representation is depicted in FIG. 4 to show the octahedral arrangement of ligands.

Specifically, the ORTEP representation of the complex $[Os(CO)_3I(FBC1)]$ with $R^1=$t-butyl; selected bond distances: Os—C1=1.883 Å, Os—C2=1.911 Å, Os—C3=1.914 Å, Os—O4=2.069 Å, Os—O5=2.092 Å, selected bond angles: Os—I1=2.722 Å, C1-Os—O4=175.09°, C2-Os—O5=176.34°, O5-Os—O4=87.74°, C3-Os—I1=179.68°.

TABLE 3

Physical properties of the iridium CVD precursors of the present invention

| Entry | Compound | M. P. (° C.) | sublim. cond. | $T_{1/2}$ (° C.)[a] | % Residue[b] |
|---|---|---|---|---|---|
| 1 | [Ir(COD)(FBC2)]; R = $CF_3$, $R^1$ = Me | 78 | 57° C./0.1 torr | 210 | 10.0 |
| 2 | [Ir(COD)(FBC2)]; R = $CF_3$, $R^1$ = Et | 111 | 50° C./0.14 torr | 193 | 17.3 |
| 3 | [Ir(COD)(FBC3)]; $R^1$ = Me | 166 | 65° C./0.1 torr | 230 | 34.5 |
| 4 | [Ir(COD)(FBC3)]; $R^1$ = n-Pr | 117 | 43° C./0.12 torr | 245 | 25.9 |
| 5 | [Ir(COD)(FBC4)]; $R^1$ = Me | 127 | 57° C./0.15 torr | 213 | 12.4 |
| 6 | [Ir(CO)$_2$(FBC2)]; R = $CF_3$, $R^1$ = n-Bu | 141 | 45° C./4 torr | 151 | 0.3 |
| 7 | [Ir(CO)$_2$(FBC3)]; $R^1$ = n-Pr | 88 | 41° C./0.8 torr | 201 | 0.9 |
| 8 | [Ir(CO)$_2$(FBC4)]; $R^1$ = Me | 104 | 42° C./3 torr | 174 | 0.1 |

[a]The temperature at which 50 wt. % of the sample has been lost during TGA analysis (heating rate = 10° C./min and $N_2$ flow rate = 100 cm$^3$/min).
[b]Total weight percent of the sample observed at 500° C. during TGA analysis.
c) Melting-point is greater than decomposition temperature.

TABLE 4

Physical properties of the ruthenium and osmium CVD precursors of the present invention

| Entry | Compound | M. P. (° C.) | sublim. cond. | $T_{1/2}$ (° C.) | % Residue |
|---|---|---|---|---|---|
| 9 | [Ru(NBD)(FBC1)$_2$], R = $CF_3$ | 82 | 45° C./0.15 torr | 157 | 3.0 |
| 10 | [Ru(COD)(FBC4)$_2$], $R^1$ = H | 288 | 150° C./0.25 torr | 288 | 19.6 |
| 11 | [Ru(COD)(FBC4)$_2$], $R^1$ = Et | 198 | 90° C./0.25 torr | 229 | 15.7 |
| 12 | [Ru(FBC2)$_3$], R = $CF_3$, $R^1$ = Me | 127 | 60° C./0.40 torr | 172 | 2.1 |
| 13 | [Ru(FBC2)$_3$], R = Me, $R^1$ = Me | 196 | 60° C./0.20 torr | 262 | 1.7 |
| 14 | [Os(CO)$_3$(CF$_3$CO$_2$)(FBC1)], R = $CF_3$ | 150 | 55° C./0.45 torr | 152 | 5.0 |
| 15 | [Os(CO)$_3$(CF$_3$CO$_2$)(FBC1)], R = t-Bu | 71 | 45° C./0.22 torr | 163 | 2.8 |
| 16 | [Os(CO)$_3$Br(FBC1)], R = t-Bu | 127 | 70° C./0.25 torr | 165 | 2.3 |
| 17 | [Os(CO)$_3$I(FBC1)], R = t-Bu | 109 | 55° C./0.12 torr | 163 | 1.2 |

D. CVD Experiments

The above-mentioned iridium, ruthenium and osmium complexes have been found to be well suited as precursors for CVD applications because they meet the following criteria: (a) they have high vapor pressure at a temperature of below 180° C., which is essential to enable a sufficient amount of the reagent vapor to be transported into the CVD reactor at the temperature convenient for CVD processing, in an inert gas or other carrier gas stream, (b) they are thermally stable below the temperature of about 180° C., and therefore do not decompose in the CVD system, and (c) they can cleanly decompose on substrates to deposit the desired composition with little or no incorporation of carbon, nitrogen and fluorine impurities.

Based on the physical data summarized in Tables 3 and 4, the CVD precursors according to this invention include the following advantages:

A. Higher thermal and oxidative stability in air.

The noble metal CVD precursors containing at least one $CF_3$ substituent can be handled in air at room temperature without showing significant decomposition.

B. Possibility of serving as a liquid CVD precursor.

Complexes 1, 7, 9 and 15 which exhibit a relatively lower melting point at below 88° C., can be used as a liquid precursor if the reservoir temperature is kept above its melting point.

C. Enhanced vapor pressure under the designated CVD conditions.

Most of these noble metal CVD precursors can be sublimed without showing significant decomposition at around 400 mtorr and at a temperature below 100° C.

D. Possibility of fine-tuning their physical properties.

The relative stability of these fluorinated chelate complexes is determined by the intrinsic bonding characteristics between the metal and the coordinative ligand. This invention provides four different types of FBC ligands that can form the required noble metal CVD precursors. Thus, selection of the best CVD precursors suited to the respective commercial processes is possible. Moreover, it is well understood that, by increasing the number of $CF_3$ substituent on the FBC ligands, the volatility of the resulting CVD precursors would improve substantially. On the other hand, increasing the chain length of the $R^1$ substituent on the nitrogen atom of the FBC ligands would reduce the volatility and decrease the melting point of the precursors.

EXPERIMENTAL SECTION

Without intending to limit it in any manner, the present invention will be further illustrated by the following examples.

Example 1

Synthesis of [Ir(COD)(FBC2)$_2$], R=$CF_3$, $R^1$=Et.

Sodium hydroxide (24 mg, 1.0 mmol) was suspended in 20 mL of THF. To this was slowly added 0.15 g of ketoimine ligand HOC(CF$_3$)=CHC(CF$_3$)=NEt (0.64 mmol) in THF (20 mL). The mixture was stirred at room temperature for 40 min. The solution was then filtered and the filtrate was transferred into a 100 mL reaction flask containing a suspension of [Ir(COD)(μ-Cl)]$_2$ (0.2 g, 0.29 mmol) in THF (50 mL). This mixture was stirred at room temperature for 4 hours, giving a dark-red solution alone with an off-white NaCl precipitate. THF was removed under vacuum and the resulting oily residue was taken into 35 mL of hexane. The solution was washed with distilled water (2×20 mL), and then treated with drying agent $Na_2SO_4$, evaporation of hexane and sublimation at 50° C. and 140 mtorr to give 0.23 g of dark red iridium compound [Ir(COD){HOC($CF_3$)=CHC($CF_3$)=NEt}] (0.43 mmol, 74%).

Spectral data: MS (EI, $^{193}$Ir), m/z 535, M$^+$. $^1$H NMR (CDCl$_3$, 333 K): δ 6.03 (s, 1H, CH), 4.48 (br, 2H, CH$_{(COD)}$), 3.44 (br, 2H, CH$_{(COD)}$), 3.39 (br, 2H, CH$_2$), 2.14~1.93 (m, 4H, CH$_{2(COD)}$), 1.53 (br, 4H, CH$_{2(COD)}$), 1.06 (t, 3H, $^3J_{HH}$=7 Hz, CH$_3$). $^{13}$C NMR (C$_6$D$_6$, 333 K): δ 164.2 (q, 1C, $^1J_{CF}$=26 Hz, CO), 164.2 (q, 1C, $^1J_{CF}$=28 Hz, CN), 120.7 (q, 1C, $^1J_{CF}$=227 Hz, CF$_3$), 120.3 (q, 1C, $^J_{CF}$=224 Hz, CF$_3$), 91.6 (s, 1C, CH), 69.9 (s, 2C, CH$_{(COD)}$), 58.1 (br, 2C, CH$_{(COD)}$), 48.8 (s, 1C, NCH$_2$), 32.6 (s, 2C, CH$_{2(COD)}$), 29.3 (s, 2C, CH$_{2(COD)}$), 20.7 (s, 1C, CH$_3$). $^{19}$F NMR (C$_6$D$_6$, 298K): δ −62.15 (s, 3F, OCCF$_3$), −73.07 (s, 3F, NCCF$_3$). Anal. Calcd. for C$_{15}$H$_{18}$F$_6$IrNO: C, 33.71; H, 3.39. Found: C, 33.47; H, 3.41.

Example 2

Synthesis of [Ir(COD)(FBC3)$_2$], R$^1$=Pr.

The preparation procedures were identical to that of example 1, using 0.2 g of [Ir(COD)(μ-Cl)]$_2$ (0.29 mmol), 0.17 g of iminoalcohol HO(CF$_3$)$_2$CH$_2$N(Me)=NPr (0.64 mmol), 0.1 g of NaOH and 50 mL of THF. For work-up, the reaction mixture was extracted with hexane, followed by drying and evaporation of hexane, the solid residue was then purified by vacuum sublimation (120 mtorr, 43° C.), giving 0.28 g of yolk yellow [Ir(COD){O(CF$_3$)$_2$CH$_2$N(Me)=NEt}] (0.50 mmol, 86%).

Spectral data: MS (EI, $^{193}$Ir), m/z 565, M$^+$. $^1$H NMR (C$_6$D$_6$, 298K): δ 4.50~4.48 (m, 2H, CH), 3.02~2.98 (m, 2H, CH), 2.80 (t, 2H, $^1J_{HH}$=8 Hz, NCH$_2$), 2.70 (s, 2H, CH$_2$), 2.23~2.10 (m, 4H, CH$_{2(COD)}$), 1.51~1.39 (m, 6H, CH$_{2(COD)}$ & NCH$_2$CH$_2$), 1.27 (s, 3H, CH$_3$), 0.64 (t, 3H, $^1J_{HH}$=7.2 Hz, NCH$_2$). $^{13}$C NMR (CDCl$_3$, 298K): δ 176.0 (s, 1C, CN), 125.5 (q, 2C, $^1J_{CF}$=292 Hz, CF$_3$), 77.1 (m, 1C, $^2J_{CF}$=28 Hz, COH), 72.3 (s, 2C, CH), 54.7 (s, 1C, NCH$_2$), 52.6 (s, 2C, CH), 45.6 (s, 1C, CH$_2$), 33.2 (s, 2C, CH$_{2(COD)}$), 30.4 (s, 2C, CH$_{2(COD)}$), 23.3 (s, 1C, NCH$_2$CH$_2$), 21.9 (s, 1C, CH$_2$), 11.1 (s, 1C, NCH$_2$CH$_2$CH$_2$). $^{19}$F NMR (C$_6$D$_6$, 298K): δ −76.15 (s, 6F, CF$_3$). Anal. Calcd. for C$_{17}$H$_{24}$F$_6$IrNO: C, 36.16; H. 4.28. Found: C, 36.17; H, 4.34.

Example 3

Synthesis of [Ir(COD)(FBC4)$_2$], R$^1$=Me.

The procedures were identical to that of example 1, using 0.2 g of [Ir(COD)(μ-Cl)]$_2$ (0.29 mmol), 0.14 g of aminoalcohol HO(CF$_3$)$_2$CH$_2$NMe$_2$ (0.64 mmol), 0.1 g of NaOH and 50 mL of THF. After removal of THF, the residue was extracted with pentane (2×20 mL), and the pentane solution was evaporated under vacuum to give 0.25 g of yellow solid [Ir(COD){O(CF$_3$)$_2$CH$_2$NMe$_2$}] (yield 82%), which was further purified by vacuum sublimation at 57° C. and 150 mtorr.

Spectral data: MS (EI, $^{193}$Ir), m/z 525, M$^+$. $^1$H NMR (C$_6$D$_6$, 298K): δ 4.48~4.45 (m, 2H, CH$_{(COD)}$), 2.72~2.69 (m, 2H, CH$_{(COD)}$), 2.39 (s, 1H, CH$_2$), 2.18~2.02 (m, 4H, CH$_{2(COD)}$), 1.80 (s, 6H, CH$_3$), 1.43~1.37 (m, 4H, CH$_{2(COD)}$). $^{13}$C NMR (CDCl$_3$, 298K): δ 124.72 (q, 2C, $^1J_{CF}$=290 Hz, CF$_3$), 88.87 (m, 1C, $^2J_{CF}$=27 Hz, CO), 67.01 (s, 2C, CH$_{(COD)}$), 65.60 (s, 1C, NCH$_2$), 54.10 (s, 2C, CH$_{(COD)}$), 50.53 (s, 2C, CH$_3$), 32.44 (s, 2C, CH$_{2(COD)}$), 30.34 (s, 2C, CH$_{2(COD)}$). $^{19}$F NMR (C$_6$D$_6$, 298K): δ −77.34 (s, 6F, CF$_3$). Anal. Calcd. for C$_{14}$H$_{20}$F$_6$IrNO: C, 32.06; H, 3.84. Found: C, 31.34; H, 3.96.

Example 4

Synthesis of [Ir(CO)$_2$(FBC4)$_2$], R$^1$=Me.

Sodium hydroxide (24 mg, 1.0 mmol) was suspended in 20 mL of THF. To this was slowly added 0.14 g of aminoalcohol HO(CF$_3$)$_2$CH$_2$NMe$_2$ (0.64 mmol) in THF (20 mL). The mixture was stirred at room temperature for 40 min. The solution was then filtered and the filtrate was transferred into a 100 mL reaction flask containing a suspension of [Ir(COD)(μ-Cl)]$_2$ (0.2 g, 0.29 mmol) in THF (20 mL). This mixture was further stirred at room temperature for 4 hours, giving a yellowish brown solution alone with an off-white NaCl precipitate. The solution was then purged with a slow stream of CO gas for 5 min., during which time the color gradually changed from brown to yellow, indicating completion of the CO substitution. The solution was filtered, the filtrate was then concentrated, and the resulting oily residue was taken into 35 mL of hexane. Evaporation of hexane and sublimation at 42° C. and 3 torr gave 0.14 g of light-yellow iridium compound [Ir(CO)$_2${O(CF$_3$)$_2$CH$_2$NMe$_2$}] (0.30 mmol, 51%).

Spectral data: MS (EI, $^{193}$Ir), m/z 473, M$^+$. $^1$H NMR (CDCl$_3$, 298K): δ 3.08 (s, 6H, N(CH$_3$)$_2$), 3.04 (s, 2H, CH$_2$). $^{13}$C NMR (CDCl$_3$, 298K): δ 171.8 (s, 1C, CO), 169.1 (s, 1C, CO), 123.6 (q, 1C, $^1J_{CF}$=348 Hz, CF$_3$), 88.3 (m, 1C, $^2J_{CF}$=29 Hz, C(CF$_3$)), 63.8 (s, 1C, NCH$_2$), 55.0 (s, 2C, CH$_3$). $^{19}$F NMR (C$_6$D$_6$, 298K): δ −76.17 (s, 6F, CF$_3$). Anal. Calcd. for C$_8$H$_8$F$_6$IrNO$_3$: C, 20.34; H, 1.71. Found: C, 20.43; H, 1.92.

Example 5

Synthesis of [Ru(NBD)(FBC1)$_2$], R=CF$_3$.

To a 100 mL reaction flask, was charged 1.0 g of [Ru(NBD)Cl$_2$]$_x$ (3.8 mmol), six equiv. of (hfac)Na (5.23 g, 22.7 mmol) and 60 mL of THF. The mixture was then heated to reflux for 20 days, during which time the solution gradually changed from brown color to red. After stopping the reaction, the solution was filtered and the filtrate was concentrated to dryness. The resulting solid residue was purified by sublimation (150 mtorr, 45° C.), giving 1.36 g of Ru(NBD)(hfac)$_2$ as red solid (2.24 mmol, 59%).

Spectral data: MS (EI, $^{102}$Ru): m/z 608 (M$^+$). $^1$H NMR: (400 MHz, CDCl$_3$, 298 K): δ 6.13 (s, 2H, CH), 5.40 (m, 2H, CH$_{(NBD)}$), 4.84 (m, 2H, CH$_{(NBD)}$), 4.04 (m, 2H, CH$_{(NBD)}$), 1.77 (s, 2H, CH$_2$). $^{13}$C NMR: (125.7 MHz, d-acetone, 298 K): δ 175.5 (q, 2C, CCF$_3$, $^2J_{CF}$=36 Hz), 175.4 (q, 2C, CCF$_3$, $^2J_{CF}$=36 Hz), 116.3 (q, 2C, CF$_3$, $^1J_{CF}$=285 Hz), 116.0 (q, 2C, CF$_3$, $^1J_{CF}$=284 Hz), 90.6 (s, 2C, CH), 82.3 (s, 2C, CH$_{(NBD)}$), 79.6 (s, 2C, CH$_{(NBD)}$), 62.3 (s, 2C, CH$_{(NBD)}$), 51.5 (s, 1C, CH$_2$). $^{19}$F (470.3 MHz, CDCl$_3$, 298 K): δ −75.13 (s, 6F, CF$_3$), −75.75 (s, 6F, CF$_3$). Anal. Calcd. for C$_{17}$H$_{10}$F$_{12}$O$_4$Ru: C, 33.62; H, 1.66. Found: C, 33.82; H, 2.15.

Example 6

Synthesis of [Ru(COD)(FBC4)$_2$], R$^1$=H.

Sodium hydride (70 mg, 3 mmol) was suspended in 20 mL of THF. To this was added dropwise 0.38 g of the aminoalcohol ligand $HOC(CF_3)_2CH_2NH_2$ (1.9 mmol) in THF (20 mL). The mixture was further stirred for 40 min. until evolution of gas had ceased. The filtrate was then transferred into a 100 mL reaction flask containing a suspension of $[Ru(COD)Cl_2]_x$ (0.15 g, 0.55 mmol) in THF solution (20 mL). This mixture was heated to reflux for 48 hours, giving a brown solution alone with an off-white NaCl precipitate. After cooling to room temperature, the mixture was filtered and the filtrate was concentrated to dryness. The solid residue was purified by column chromatography on silica gel using ethyl acetate as eluent and the resulting orange solid was then sublimed under vacuum (250 mtorr, 150° C.), giving 0.23 g of light yellow $[Ru(COD)\{OC(CF_3)_2 CH_2NH_2\}_2]$ (0.38 mmol, 70%).

Spectral data: MS (EI, $^{102}$Ru): m/z 602 (M$^+$). $^1$H NMR (300 MHz, d-acetone, 298 K): δ 5.37 (s, 2H, NH), 5.18 (s, 2H, NH), 3.63 (m, 4H, NCH$_2$), 3.38 (m, 2H, CH$_{(COD)}$), 3.30 (m, 2H, CH$_{(COD)}$), 2.51 (m, 2H, CH$_{2(COD)}$), 2.30 (m, 2H, CH$_{2(COD)}$), 2.15 (m, 2H, CH$_{2(COD)}$), 1.81 (m, 2H, CH$_{2(COD)}$). $^{13}$C NMR (125.7 MHz, d-acetone, 298 K): δ 124.9 (q, 2C, CF$_3$, $^1J_{CF}$=296 Hz), 124.6 (q, 2C, CF$_3$, $^1J_{CF}$=292 Hz), 83.2 (m, 2C, C(CF$_3$)$_2$, $^2J_{CF}$=26 Hz), 79.4 (s, 2C, CH$_{(COD)}$), 76.5 (s, 2C, CH$_{(COD)}$), 52.2 (s, 2C, NCH$_2$), 30.3 (s, 2C, CH$_{2(COD)}$), 28.3 (s, 2C, CH$_{2(COD)}$). $^{19}$F (470.3 MHz, acetone-d$_6$, 298 K): δ −76.60 (s, 6F, CF$_3$), −76.62 (s, 6F, CF$_3$). Anal. Calcd. for $C_{16}H_{20}F_{12}N_2O_2Ru$: C, 31.95; H, 3.35; N, 4.66. Found: C, 32.12; H, 3.80; N, 4.60.

Example 7

Synthesis of [Ru(COD)(FBC4)$_2$], R$^1$=Et.

The procedures were identical to that of example 6, using 0.46 g of $[Ru(COD)Cl_2]_x$ (1.7 mmol), 1.03 g of aminoalcohol ligand $HOC(CF_3)_2CH_2NHEt$ (4.58 mmol) and slightly excess of sodium hydride. After removal of solvent, the solid residue was then purified by column chromatography on silica gel using a 2:1 mixture of hexane and CH$_2$Cl$_2$ as eluent and the resulting orange solid was sublimed under vacuum (250 mtorr, 90° C.), giving 0.85 g of orange [Ru(COD){OC(CF$_3$)$_2$CH$_2$NHEt}$_2$] (1.29 mmol, 76%).

Spectral data: MS (EI, $^{102}$Ru): m/z 658 (M$^+$). $^1$H NMR (400 MHz, CDCl$_3$, 298 K): δ 4.09 (m, 2H, CH$_{(COD)}$), 3.69 (m, 2H, CH$_{(COD)}$), 3.47 (m, 2H, CH$_2$CH$_3$, $^3J_{HH}$=7.2 Hz), 3.40 (m, 2H, NCH$_2$), 2.80 (s, 2H, NH), 2.66 (m, 2H, NCH$_2$), 2.53 (m, 2H, CH$_{2(COD)}$), 2.20 (m, 2H, CH$_{2(COD)}$), 2.08 (m, 2H, CH$_2$CH$_3$, $^3J_{HH}$=7.2 Hz), 2.06 (m, 2H, CH$_{2(COD)}$), 1.81 (m, 2H, CH$_{2(COD)}$), 1.17 (t, 6H, CH$_3$, $^3J_{HH}$=7.2 Hz). $^{13}$C NMR (125.7 MHz, CDCl$_3$, 298 K): δ 125.4 (q, 2C, CF$_3$, $^1J_{CF}$=293 Hz), 124.1 (q, 2C, CF$_3$, $^1J_{CF}$=291 Hz), 93.9 (s, 2C, CH$_{(COD)}$), 85.4 (m, 2C, C(CF$_3$)$_2$, $^2J_{CF}$=27 Hz), 82.2 (s, 2C, CH$_{(COD)}$), 53.8 (s, 2C, NCH$_2$), 45.9 (s, 2C, CH$_2$CH$_3$), 30.9 (s, 2C, CH$_{2(COD)}$), 27.2 (s, 2C, CH$_{2(COD)}$), 13.9 (s, 2C, CH$_3$) $^{19}$F (470.3 MHz, CDCl$_3$, 298 K): δ −76.81 (q, 6F, CF$_3$, $^4J_{FF}$=10.8 Hz), −77.50 (q, 6F, CF$_3$, $^4J_{FF}$=10.8 Hz). Anal. Calcd. for $C_{20}H_{28}F_{12}N_2O_2Ru$: C, 36.53; H, 4.29; N, 4.26. Found: C, 36.42; H, 4.30; N, 4.44.

Example 8

Synthesis of [Ru(FBC2)$_3$], R=CF$_3$, R$^1$=Me.

Sodium hydride (50 mg, 2.08 mmol) was suspended in 20 mL of THF. To this was added dropwise 0.38 g of the β-ketoimine ligand HOC(CF$_3$)=CHC(CF$_3$)=NMe, (hfim, 1.72 mmol) in THF (20 mL). The mixture was stirred for 40 min. at room temperature until evolution of gas had ceased. The solution was then filtered to remove the excess NaH, and filtrate was transferred into a 100 mL reaction flask containing a suspension of $[Ru(COD)Cl_2]_x$ (0.15 g, 0.54 mmol) in THF solution (60 mL). This mixture was heated to reflux for 48 hours, giving a dark-green solution along with an off-white NaCl precipitate. After allowing the solution to cool to room temperature, the mixture was filtered and the filtrate was concentrated to dryness. The solid residue was purified by column chromatography on silica gel eluting with a 1:3 mixture of CH$_2$Cl$_2$ and hexane, giving 0.23 g of [Ru(hfim)$_3$] (0.30 mmol, 56%) as green solid. Further purification was carried out using sublimation at 60° C./400 mtorr, m.p.=127° C.

Selected data: MS (EI, 70 eV, L=C$_6$H$_4$F$_6$NO), observed (actual) [assignment]: 762 (762) [RuL$_3$], 541 (541) [[RuL$_2$], 321 (321) [RuL], 220 (220) [L]. Anal. calcd. for $C_{18}H_{12}F_{18}N_3O_3Ru$: C, 28.40; H, 1.59; N, 5.52. Found: C, 28.75; H, 1.79; N, 5.23.

Example 9

Synthesis of [Ru(FBC2)$_3$], R=Me, R$^1$=Me.

The synthetic procedures were essentially identical to that of example 8, using 0.40 g of $[Ru(COD)Cl_2]_x$ (1.45 mmol), 0.84 g of the β-ketoimine ligand HOC(CF$_3$)=CHC(Me)= NMe (tfim, 5.02 mmol) and 0.16 g of NaH (6.7 mmol) in 80 mL of THF. After stopping the reaction and removal of the solvent, the resulting solid residue was purified by column chromatography on silica gel eluting with a 1:1 mixture of CH$_2$Cl$_2$ and hexane, giving 0.51 g of [Ru(tfim)$_3$] (0.85 mmol, 59%) as red solid. Further purification was carried out using sublimation at 60° C./200 mtorr, m.p.=195° C.

Selected data: MS (EI, 70 ev, L=C$_6$H$_6$F$_3$NO), observed (actual) [assignment]: 600 (600) [RuL$_3$], 433 (433) [[RuL$_2$], 265 (267) [RuL], 166 (166) [L]. Anal. Calcd. for $C_{18}H_{21}F_9N_3O_3Ru$: C, 36.07, H, 3.53, N, 7.01. Found: C, 36.11, H, 3.90, N, 6.98.

Example 10

Synthesis of [Os(CO)$_3$(CF$_3$CO$_2$)(FBC1)], R=CF$_3$.

Finely crushed [Os(CO)$_3$(CF$_3$CO$_2$)]$_2$ (0.2 g, 0.26 mmol) and β-diketonate ligand (hfac)H (0.32 g, 1.55 mmol) in a 18 mL Carius tube were degassed and the tube sealed under vacuum. After heated at 185° C. for 6 hours, the tube was then cooled and opened. The reaction mixture was extracted with CH$_2$Cl$_2$ to give a yellow-cream solid. Further purification by vacuum sublimation gave [Os(CO)$_3$(CF$_3$CO$_2$)(hfac)] as light yellow solid (0.24 g, 0.40 mmol) yield: 77%.

Spectral data: MS (EI, $^{192}$Os): m/z 483 (M$^+$−C$_2$O$_2$F$_3$). IR (C$_6$H$_{12}$): ν (CO), 2142 (vs), 2066 (vs), 2057 (vs) cm$^{-1}$. $^1$H NMR (400 MHz, acetone-d$_6$, 298K): δ 6.76 (s, 1H, CH). $^{13}$C NMR (75 MHz, acetone-d$_6$, 298K): δ 176.0 (q, 1C, $^2J_{CF}$=38 Hz, C(CF$_3$)), 166.8 (1C, CO), 164.6 (2C, CO), 161.7 (q, 1C, $^2J_{CF}$=38 Hz, C(CF$_3$)), 117.0 (q, 2C, $^1J_{CF}$=283 Hz, CF$_3$), 115.1(1C, q, $^1J_{CF}$=283 Hz, CF$_3$), 94.4(1C, CH). $^{19}$F NMR (470 MHz, acetone-d$_6$, 298K): δ −74.07 (s, 3F), −74.61 (s, 6F). Anal. Calcd for $C_{10}HF_9O_7Os$: C, 20.21; H, 0.17. Found: C, 20.25; H, 0.25.

Example 11

Synthesis of [Os(CO)$_3$(CF$_3$CO$_2$)(FBC1)], R=t-Bu.

Finely crushed [Os(CO)$_3$(CF$_3$CO$_2$)]$_2$ (0.5 g, 0.65 mmol) and (tdhd)H ligand (1,1,1-trifluoro-5,5-dimethyl-2,4-hexanedione, 0.76 g, 3.87 mmol) in a 18 mL Carius tube were degassed and the tube sealed under vacuum. After heated at 185° C. for 6 hours, the tube was then cooled and opened. The reaction mixture was extracted with $CH_2Cl_2$ to give a yellow-cream solid. Further purification by vacuum sublimation (220 mtorr, 45° C.) gave $[Os(CO)_3(CF_3CO_2)(tdhd)]$ as light yellow solid (0.59 g, 1.01 mmol) yield: 78%. Single crystals were grown from a 1:1 mixture of $CH_2Cl_2$ and hexane at room temperature.

Spectral data: MS (EI, $^{192}$Os), m/z 584 (M$^+$). IR ($C_6H_{12}$): ν (CO), 2132 (vs), 2057 (vs), 2040 (vs) cm$^{-1}$. $^1$H NMR (400 MHz, $CDCl_3$, 294K): δ 6.23 (s, 1H, CH), 1.19 (s, 9H, $^t$Bu). $^{13}$C NMR (100 MHz, $CDCl_3$, 294K): δ 207.4 (1C, C(CF$_3$)), 169.0 (q, 1C, $^2J_{CF}$=35 Hz, C(CF$_3$)), 168.2 (1C, CO), 165.6 (1C, CO), 165.1 (1C, CO), 162.3 (q, 1C, $^2J_{CF}$=38 Hz, C(CF$_3$)), 117.6 (q, 1C, $^1J_{CF}$=281 Hz, CF$_3$), 114.7(q, 1C, $^1J_{CF}$=286 Hz, CF$_3$), 94.3 (1C, CH), 43.4 (1C, CMe$_3$), 27.4 (3C, Me). $^{19}$F NMR (470.3 MHz, $CDCl_3$, 298K): δ −74.46 (s, 3F), −74.51 (s, 3F). Anal. Calcd for $C_{13}H_{10}F_6O_7Os$: C, 26.81; H, 1.73. Found: C, 26.96; H, 2.19.

Example 12

Synthesis of [Os(CO)$_3$Br(FBC1)], R=t-Bu.

Finely crushed $[Os(CO)_3(\mu\text{-Br})]_2$ (0.1 g, 0.13 mmol) and (tdhd)H (0.15 g, 0.77 mmol) in a 10 mL Carius tube were degassed and the tube sealed under vacuum. After heated at 185° C. for 6 hours, the tube was then cooled and opened. The reaction mixture was extracted with $CH_2Cl_2$ to give a yellow-cream solid. Further purification by vacuum sublimation (250 mtorr, 70° C.) gave [Os(CO)$_3$Br(tdhd)] as light yellow solid (0.10 g, 0.19 mmol), yield: 73%. Single crystals were grown from a 1:1 mixture of $CH_2Cl_2$ and hexane at room temperature.

Spectral data: MS (EI, $^{192}$Os), m/z 550 (M$^+$). IR ($C_6H_{12}$): ν (CO), 2123 (s), 2047 (vs), 2030 (vs) cm$^{-1}$. $^1$H NMR (400 MHz, $CDCl_3$, 294K): δ 6.19 (s, 1H, CH), 1.21 (s, 9H, $^t$Bu). $^{13}$C NMR (100 MHz, $CDCl_3$, 294K): δ 206.6 (1C, CO), 168.5 (q, 1C, $^2J_{CF}$=34 Hz, C(CF$_3$)), 166.7 (1C, CO), 166.3 (1C, CO), 165.2 (1C, CO), 117.4 (q, 1C, $^1J_{CF}$=283 Hz, CF$_3$), 94.9 (1C, CH), 43.0 (1C, CMe$_3$), 27.5 (3C, Me). $^{19}$F NMR (470.3 MHz, $CDCl_3$, 298K): δ −74.75 (s, 3F). Anal. Calcd for $C_{11}H_{10}BrF_3O_5Os$: C, 24.05; H, 1.83. Found: C, 22.84; H, 2.61.

Example 13

Synthesis of [Os(CO)$_3$I(FBC1)], R=t-Bu.

Finely crushed $[Os(CO)_3(\mu\text{-I})]_2$ (0.1 g, 0.11 mmol) and (tdhd)H (0.13 g, 0.69 mmol) in a 10 mL Carius tube were degassed and the tube sealed under vacuum. After heated at 185° C. for 6 hours, the tube was then cooled and opened. The reaction mixture was extracted with $CH_2Cl_2$ to give a yellow solid. Further purification by vacuum sublimation (120 mtorr, 55° C.) gave [Os(CO)$_3$I(tdhd)] as light yellow solid (0.10 g, 0.17 mmol), yield: 76%. Single crystals were grown from a 1:1 mixture of $CH_2Cl_2$ and hexane at room temperature.

Spectral data: MS (EI, $^{192}$Os), m/z 598 (M$^+$). IR ($C_6H_{12}$): ν (CO), 2119 (s), 2044 (vs), 2030 (vs) cm$^{-1}$. $^1$H NMR (400 MHz, $CDCl_3$, 294K): δ 6.20 (s, 1H, CH), 1.20 (s, 9H, $^t$Bu). $^{13}$C NMR (100 MHz, $CDCl_3$, 294K): δ 206.7 (1C, CO), 168.6 (q, 1C, $^2J_{CF}$=33 Hz, C(CF$_3$)), 167.3 (1C, CO), 166.9 (1C, CO), 163.7 (1C, CO), 117.2 (q, 1C, $^1J_{CF}$=272 Hz, CF$_3$), 95.6 (1C, CH), 42.8 (1C, CMe$_3$), 27.5 (3C, Me). $^{19}$F NMR (470.3 MHz, $CDCl_3$, 298K): δ −74.86 (s, 3F). Anal. Calcd for $C_{11}H_{10}F_3IO_5Os$: C, 22.16; H, 1.69. Found: C, 26.64; H, 2.13.

Example 14

CVD of the Corresponding Metal Thin-film

Typically, the iridium, ruthenium and osmium thin-films may be prepared by chemical vapor deposition at about 300–500° C. and about 400–2000 mtorr in a typical cold-wall reactor. In this example, the complexes 2, 4~8 and 11~14 were used as the source reagents and the run conditions are listed in Tables 5 and 6. Growth of smooth metallic thin films was realized on Si wafer and Pyrex glass substrates. The deposited films were found to be highly reflective with good adhesion to all substrates. The composition of the films was determined by Auger/ESCA analysis. The electrical resistivity of films was measured by a four-point probe method at room temperature.

TABLE 5

Selected CVD parameters for experiments using iridium complexes as source reagents and pyrex glass and Si wafer as substrates

| Compound | CG$_{FR}$ (sccm) | T$_R$ (° C.) | T$_D$ (° C.) | R$_D$ (Å/min) | Contents (at. %) and Resistivity ρ (μΩ-cm) |
|---|---|---|---|---|---|
| 2 | O$_2$ (40 sccm) | 80 | 400 | 70 | Ir, 98%; O, 2%. ρ = 10.2. |
| 4 | O$_2$ (20 sccm) | 80 | 375 | 38 | Ir, 99%; O, 1%. ρ = 8.4. |
| 5 | O$_2$ (20 sccm) | 80 | 350 | 53 | Ir, 98%; O, 2%. ρ = 9.6. |
| 6 | O$_2$ (20 sccm) | 70 | 400 | 110 | Ir, 96%; O, 4%. ρ = 19.3. |
| 7 | O$_2$ (20 sccm) | 70 | 350 | 66 | Ir, 99%; O, 1%. ρ = 6.8. |
| 8 | O$_2$ (20 sccm) | 70 | 400 | 68 | Ir, 97%; C, 1%; O, 2%. ρ = 13.9. |

Compound number is identical to those of the entry number listed in Tables 3 and 4.
Abbreviations:
CG$_{FR}$ = carrier gas flow rate,
T$_R$ = temperature of precursor reservoir,
T$_D$ = deposition temperature and
R$_D$ = deposition rate.

TABLE 6

Selected CVD parameters for experiments using ruthenium or osmium complexes as source reagents and pyrex glass and Si wafer as substrates

| Compound | $CG_{FR}$ (sccm) | $P_S$ (torr) | $T_R$ (° C.) | $T_D$ (° C.) | $R_D$ (Å/min) | Contents (at. %) and Resistivity $\rho$ ($\mu\Omega$-cm) |
|---|---|---|---|---|---|---|
| 9  | $H_2$ (10 sccm)     | 2    | 55  | 450 | 30  | Ru, 94.5%; C, 2.5%; O, 3%. $\rho = 14.1$. |
| 11 | $O_2$/Ar (10 sccm)  | 0.25 | 110 | 425 | 14  | Ru, 59%; C, 41%. $\rho = 10.2$. |
| 12 | $O_2$/Ar (15 sccm)  | 1    | 80  | 450 | 30  | Ru, 94.8%; O, 5.2%. $\rho = 10.5$. |
| 12 | $O_2$ (20 sccm)     | 2    | 70  | 325 | 21  | $\rho = 201.0$. |
| 13 | $O_2$/Ar (30 sccm)  | 0.5  | 130 | 425 | 17  | Ru, 98%; C, 0.2%; O, 1.8%. $\rho = 14.5$ |
| 13 | $O_2$ (50 sccm)     | 0.5  | 130 | 425 | 114 | $\rho = 151.4$ |
| 14 | $H_2$ (15 sccm)     | 1    | 90  | 400 | 100 | Os, 96%; C, 3%; O, 1%. $\rho = 31.0$. |

Compound number is identical to those of the entry number listed in Tables 3 and 4.
Abbreviations:
$CG_{FR}$ = carrier gas flow rate,
$P_S$ (torr) = system pressure,
$T_R$ = temperature of precursor reservoir,
$T_D$ = deposition temperature and
$R_D$ = deposition rate.

The invention claimed is:

1. A noble metal organometallic complex of general formula (I):

$$[ML_aX_b(FBC)_c] \quad (I)$$

wherein M is a noble metal; L is a neutral ligand selected from the group consisting of carbonyl, alkene, diene and derivatives of alkenes and dienes additionally containing alkyl or fluorinated alkyl substituents; X Is an anionic ligand; wherein a is an integer of from zero (0) to three (3), b is an integer of from zero (0) to one (1) and c is an integer of from one (1) to three (3); FBC ligand is a fluorinated bidentate chelate ligand selected from the group consisting of a beta-ketoiminate (FBC2), imino-alcoholate (FBC3) and amino-alcoholate (FBC4) having the structural formula indicated below:

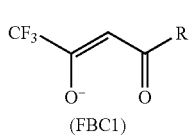
(FBC1)
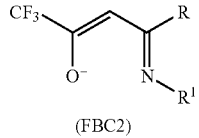
(FBC2)
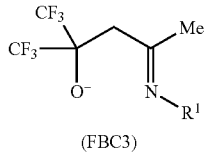
(FBC3)
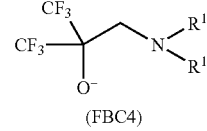
(FBC4)

wherein R is a C1–C4 alkyl or trifluoromethyl; $R^1$ is a C1–C6 alkyl group, which may be substituted by a C1–C4 alkoxy group, and wherein FBC4, one of the $R^1$ groups may be H.

2. A compound according to claim 1, wherein the anionic ligand is chloride, bromide, iodide or trifluoroacetate.

3. A compound according to claim 2, wherein R is methyl, t-butyl or trifluoromethyl.

4. A compound according to claim 3, wherein $R^1$ is methyl, ethyl, allyl, n-propyl, i-propyl, n-butyl, i-butyl or 2-methoxyethyl.

5. A compound according to claim 1, wherein the noble metal is selected from the group consisting of iridium, ruthenium and osmium.

6. A compound according to claim 5, wherein the transition metal is iridium.

7. A compound selected from the group consisting of

$$[IrL_a(FBC2)] \quad (II),$$

$$[IrL_a(FBC3)] \quad (III)$$

and

$$[IrL_a(FBC4)] \quad (IV)$$

wherein L is a neutral ligand selected from the group consisting of carbonyl, alkene, diene or derivatives of alkenes and dienes additionally containing at least one alkyl or fluorinated alkyl substituent; a is an integer of one or two, depending on the donor bonding of the selected ligand; FBC ligand is a fluorinated bidentate chelate ligand selected from the group consisting of beta-keloiminate, imino-alcoholate (FBC3) and amino-alcoholate (FBC4) having the structural formula indicated below:

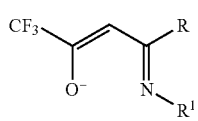
(FBC2)
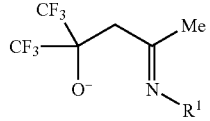
(FBC3)
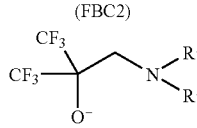
(FBC4)

wherein R is C1–C4 alkyl or trifluoromethyl; $R^1$ is C1–C6 alkyl, which may be substituted by a C1–C4 alkoxy group, and wherein FBC4, one of the $R^1$ groups may be H.

8. A compound according to claim 7, wherein R is methyl, t-butyl or trifluoromethyl.

9. A compound according to claim 8, wherein $R^1$ is methyl, ethyl, allyl, n-propyl, i-propyl, n-butyl, i-butyl or 2-methoxyethyl.

10. A compound selected from the group consisting of

[RuL$_a$(FBC1)$_2$]     (V),

[RuL$_a$(FBC4)$_2$]     (VI)

and

[RuL$_a$(FBC2)$_3$]     (VII)

wherein L is a neutral ligand selected from the group consisting of a cyclic diene selected from COD and NBD, or derivatives of a cyclic diene additionally containing at least one alkyl or fluorinated alkyl substituent; a is one or zero, depending on the (FBC) ligand selected for the reactions; FBC ligand is a fluorinated bidentate chelate ligand selected from the group consisting of beta-diketonate (FBC1), beta-ketoiminate (FBC2) and amino-alcoholate (FBC4) having structural formula indicated below:

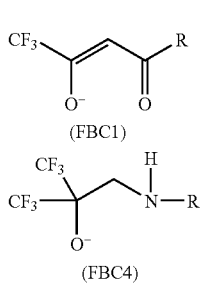

wherein R is C1–C4 alkyl, or trifluoromethyl; $R^1$ is a C1–C6 alkyl group, which may be substituted by a C1–C4 alkoxy group, and wherein (FBC4), $R^1$ may be H.

11. A compound according to claim 10, wherein R is methyl, t-butyl or trifluromethyl.

12. A compound according to claim 11, wherein $R^1$ is methyl, ethyl, allyl, n-propyl, i-propyl, n-butyl, i-butyl or 2-methoxyethyl.

13. A compound of the general formula VIII

[OsL$_a$X(FBC)]     (VIII)

wherein L represents carbonyl ligand; a has a constant value of three (3), X is an anionic monodentate ligand; FBC ligand is a fluorinated bidentate chelate ligand selected from: (hfac)=hexafluoroacetylacetonate, (tfac)=trifluoroacetylacetonate, and (tdhd)=1,1,1-trifluoro-5,5-dimethyl-2,4-hexanedionate.

14. A compound according to claim 13, wherein X is chloride, bromide, iodide or trifluoroacetate.

15. A method for making a noble metal organometallic complex of general formula (I) as defined in claim 1, comprising (a) reacting the respective FBC ligand with a suitable metal hydride, followed by (b) treatment of the product so formed with a metal halide salt of the desired metal.

16. A method according to claim 15, wherein the metal hydride is sodium hydride.

17. A method according to claim 16, wherein the metal halide salt is [Ir(COD)(μ-Cl)]$_2$ wherein COD=1,5-cyclooctadiene; [Os(CO)$_3$(μ-X)]$_2$ wherein X=CF$_3$CO$_2$, Cl, Br or I; [Ru(CO)Cl$_2$]$_x$ wherein COD=1,5-cyclooctadiene; and [Ru(NBD)Cl$_2$]$_x$, wherein NBD=2,5-norbornadiene.

18. A method for the chemical vapor deposition of a thin film of a noble metal on a substrate, wherein the thin film is formed on the substrate by depositing a compound of formula I as defined in claim 1, under an inert gas atmosphere, wherein the inert gas is selected from the group consisting of N$_2$, He and Ar.

19. A method according to claim 18, wherein the noble metal is selected from the group consisting of iridium, ruthenium and osmium.

20. A method according to claim 18, and wherein the noble metal thin film is converted to a thin film selected from the group consisting of IrO$_2$, RuO$_2$ and OsO$_2$.

21. A method for the chemical vapor deposition of a thin film of a noble metal on a substrate, wherein the thin film is formed on the substrate by depositing a compound of formula I as defined in claim 1 in the presence of H$_2$.

* * * * *